United States Patent
Clancy et al.

(10) Patent No.: US 9,955,906 B2
(45) Date of Patent: May 1, 2018

(54) SYSTEM AND METHOD FOR SELECTING AN AUDIO FILE USING MOTION SENSOR DATA

(71) Applicant: Beats Medical Limited, Dublin (IE)

(72) Inventors: Ciara Lourda Clancy, Dublin (IE); Cianan Colm Clancy, Skerries (IE); Wui Mei Chew, Dublin (IE)

(73) Assignee: Beats Medical Limited, Dublin (IE)

( * ) Notice: Subject to any disclaimer, the term of this patent is extended or adjusted under 35 U.S.C. 154(b) by 0 days. days.

(21) Appl. No.: 15/035,231

(22) PCT Filed: Nov. 10, 2014

(86) PCT No.: PCT/EP2014/074173
§ 371 (c)(1),
(2) Date: May 7, 2016

(87) PCT Pub. No.: WO2015/067801
PCT Pub. Date: May 14, 2015

(65) Prior Publication Data
US 2016/0270712 A1   Sep. 22, 2016

(30) Foreign Application Priority Data
Nov. 8, 2013   (EP) ..................................... 13192205

(51) Int. Cl.
*G06F 17/00*    (2006.01)
*A61B 5/00*    (2006.01)
(Continued)

(52) U.S. Cl.
CPC .......... *A61B 5/4082* (2013.01); *A61B 5/0022* (2013.01); *A61B 5/112* (2013.01);
(Continued)

(58) Field of Classification Search
CPC ..... A61B 5/7285; A61B 5/112; A61B 5/6898; A61B 5/4082; A61B 2562/0219
See application file for complete search history.

(56) References Cited

U.S. PATENT DOCUMENTS

2002/0107556 A1* 8/2002 Mcloul .................... A61H 1/00
                                                              607/48
2003/0167908 A1    9/2003 Nishitani et al.
(Continued)

FOREIGN PATENT DOCUMENTS

CN    201 631 999 U    11/2010
JP    2007 516519 A     6/2007

OTHER PUBLICATIONS

Wijnalda, G. et al"A Personalized Music System for Motivation in Sports Performance" IEEE Pervasive Computing, IEEE Service Center, Los Alamitos, CA, US, vol. 4 No. 3 Jul. 1, 2005.

*Primary Examiner* — Andrew C Flanders
(74) *Attorney, Agent, or Firm* — LaMorte & Associates P.C.

(57) ABSTRACT

The present invention relates to a system and a method for selecting an audio file using motion data from a mobile computing device connected to or held by a user, the mobile computing device comprising or coupled to motion sensors. The method comprising steps of moving the mobile computing device, obtaining motion data from the motion sensors, computing from the motion data step data based on a number of steps taken by the user in a specific period of time, computing a metronome beat based on the step data and generating a metronome beat file, selecting a stored audio file having a predefined beat parameter matching the metronome beat of the metronome beat file, and playing the audio file. The present invention provides a technology solution delivered through a mobile computing device, such as smart phone, or other computing device, such as a laptop
(Continued)

or a PC, a wrist or smart watch, or an accelerometer, pedometer or other external computing device having computer processor means, that improves the gait of people with Parkinson's disease. In use, the user's daily mobility is assessed through application software on a mobile computing device which is operable to calculate a required individually prescribed treatment for a user. The treatment is then delivered through speakers of the mobile computing device in the form of metronome therapy which is form of auditory cueing that is used to treat people with Parkinson's disease.

15 Claims, 18 Drawing Sheets

(51) Int. Cl.
    *A61B 5/11*     (2006.01)
    *G10H 1/40*     (2006.01)
    *G06F 3/0346*     (2013.01)
    *G10H 1/00*     (2006.01)
    *G06F 3/16*     (2006.01)

(52) U.S. Cl.
    CPC .......... *A61B 5/6898* (2013.01); *A61B 5/7282* (2013.01); *G06F 3/0346* (2013.01); *G10H 1/0008* (2013.01); *G10H 1/40* (2013.01); *A61B 2560/0223* (2013.01); *A61B 2562/0219* (2013.01); *G06F 3/162* (2013.01); *G10H 2220/086* (2013.01); *G10H 2220/395* (2013.01); *G10H 2230/015* (2013.01); *G10H 2240/135* (2013.01)

(56) References Cited

U.S. PATENT DOCUMENTS

| | | | |
|---|---|---|---|
| 2004/0204635 A1* | 10/2004 | Scharf | A61B 5/0002 600/323 |
| 2005/0128067 A1 | 6/2005 | Zakrewski | |
| 2006/0253210 A1* | 11/2006 | Rosenberg | G11B 27/005 700/94 |
| 2007/0169614 A1* | 7/2007 | Sasaki | A63B 69/0028 84/612 |
| 2007/0254271 A1 | 11/2007 | Burlik et al. | |
| 2007/0270667 A1 | 11/2007 | Coppi et al. | |
| 2008/0092723 A1 | 4/2008 | Sawyer-Kovelman et al. | |
| 2008/0153671 A1 | 6/2008 | Ogg et al. | |
| 2008/0250914 A1* | 10/2008 | Reinhart | G10H 1/0025 84/645 |
| 2009/0024233 A1* | 1/2009 | Shirai | G06F 19/3481 700/94 |
| 2010/0075806 A1* | 3/2010 | Montgomery | A63B 24/0003 482/8 |
| 2011/0184225 A1* | 7/2011 | Whitall | A63B 69/0028 600/28 |
| 2013/0041617 A1 | 2/2013 | Pease et al. | |
| 2013/0228063 A1 | 9/2013 | Turner | |

* cited by examiner

SYSTEM AND METHOD FOR SELECTING AN AUDIO FILE USING MOTION SENSOR DATA

The present invention relates to a system and method for selecting an audio file using motion sensor data.

There are more than six million people worldwide with Parkinson's disease (PD). People with PD suffer from dysfunction of the basal ganglia and this dysfunction leads to the debilitating symptoms experienced by people with PD, including decreased walking velocity, developing a shuffling walk and episodes where walking may freeze completely, known as freezing of gait (FOG).

It is an object of the present invention to provide a system and method for overriding the dysfunction of the basal ganglia in the brain of a PD sufferer and to generate and deliver to the PD sufferer auditory cues for overcoming PD symptoms externally so as to improve the quality of walking and prevent freezing episodes.

Further aspects of the present invention will become apparent from the ensuing description which is given by way of example only.

According to the invention, there is provided a method for selecting an audio file using motion data from a mobile computing device, the mobile computing device connected to or held by a user and comprising or coupled to motion sensors operable to detect motion of the user, the method comprising steps of:
  setting a sensitivity level for the motion sensors such that the motion sensors are operable to detect when a step is made by the user;
  obtaining motion data from the motion sensors;
  computing from the motion data step data based on a number of steps taken by the user in a specific period of time;
  setting a sensitivity level for the motion sensors such that the motion sensors are operable to detect when a step is made by the user;
  computing a metronome beat based on the step data and generating a metronome beat file;
  selecting a stored audio file having a predefined beat parameter matching the metronome beat of the metronome beat file, and
  playing the audio file on audio output means so that the audio file is heard by the user.

In another embodiment of the invention, the step of setting a sensitivity level for the motion sensors comprises calibrating the motion sensors to detect steps of a user according to one or more of stride length, speed and cadence. The ability to adapt the sensitivity of the motion sensors in this way ensures that the present invention may be adapted to the specific gait requirements of a user so that steps having a smaller (or indeed larger) amplitude and/or stride length from a pre-determined level may be correctly sensed, which is important for patients suffering from Parkinson's disease.

Preferably, the step of setting a sensitivity level for the motion sensors is performed automatically by the mobile computing device.

Preferably, the method comprises the further step of: using the motion sensors to detect a change in the motion of the user, and using the detected change of motion to determine whether the user is suffering from a motion event relating to Parkinson's disease.

Such a step involves detecting the deceleration rate of motion of the user, and then comparing the detected deceleration rate to a predetermined range of deceleration rates and if the detected deceleration rate falls within the predetermined range recording motion data relating to the detected deceleration. Such a motion event would indicate that the user has suffered a true Parkinson's freezing event, or alternatively if the detected deceleration rate falls outside the predetermined range, that the user has stopped stepping for other reasons not related to Parkinson's disease.

In another embodiment of the invention, the step of generating a metronome beat file is performed at a remote computing device or by the mobile computing device.

Preferably, the step of computing a metronome beat based on the step data comprises a step of applying a multiplication factor to the step data obtained before a metronome beat file is generated.

Preferably, the metronome beat and predefined beat parameter is measured in beats per minute.

Preferably, a plurality of audio files, each having a different predefined beat parameter, is stored in storage means of the mobile computing device or a remote external storage means.

In another embodiment of the invention, the method comprises a step of receiving audio files at or downloading audio files to the mobile computing device.

Alternatively, the audio files are stored in storage means of a remote computing device.

In another embodiment of the invention, the audio files have beat parameters in the range of 5 beats per minute to 300 beats per minute, although it will be understood that audio files may be provided in any range as required or as desired.

In another embodiment of the invention, the method comprises the further step of transmitting the step data and/or metronome beat to a remote computing device.

In another embodiment of the invention, the motion sensors comprise an accelerometer and/or a gyroscope.

Preferably, the mobile computing device is a mobile phone with a computing processor, such as a smart phone or other computing device, such as a laptop or a PC, a wrist or smart watch, or an external device, such as an accelerometer, a pedometer or other external device having computer processor means.

Preferably, the remote computing device is a computer server.

According to a further aspect of the invention, there is provided a system for selecting an audio file using motion data from a mobile computing device connected to or held by a user, the system comprising:
  at least one mobile computing device comprising or coupled to motion sensors;
  means for setting a sensitivity level for the motion sensors such that the motion sensors are operable to detect when a step is taken by the user;
  means for obtaining motion data from the motion sensors;
  means for computing from the motion data step data based on a number of steps taken by a user in a specific period of time;
  means for computing a metronome beat based on the step data and generating a metronome beat file;
  means for selecting a stored audio file having a predefined beat parameter matching the metronome beat of the metronome beat file, and
  audio output means for playing the audio file so that the audio file is heard by the user.

Preferably, the means for setting a sensitivity level for the motion sensors comprises means for calibrating the motion sensors to detect steps of a user according to one or more of stride length, speed and cadence.

Preferably, the system comprises means for setting a sensitivity level for the motion sensors is performed automatically by the mobile computing device.

Preferably, the motion sensors are operable to detect a change in the motion of the user, whereby the detected change of motion is used to determine whether the user is suffering from a motion event relating to Parkinson's disease.

Preferably, the motion sensors are operable to detect deceleration of motion of the user, the system comprising means for comparing the detected deceleration to a predetermined range and if the detected deceleration falls within the predetermined range the system is operable to record motion data relating to the detected deceleration.

Preferably, the system comprises means for generating a metronome beat file at a remote computing device or by the mobile computing device.

Preferably, the system comprises means for applying a multiplication factor to the step data obtained before a metronome beat file is generated.

Preferably, the metronome beat and predefined beat parameter is measured in beats per minute.

Preferably, the system comprises storage means for storing a plurality of audio files, each having a different predefined beat parameter.

Preferably, the system comprises means for receiving audio files at or downloading audio files to the mobile computing device.

Preferably, the system comprises means for transmitting the step data and/or metronome beat to a remote computing device.

Preferably, the system comprises an accelerometer and/or a gyroscope to detect the motion of the user.

Preferably, the accelerometer comprises means to detect 3-axis acceleration, deceleration or movement of the user.

Preferably, the mobile computing device is a mobile phone with a computing processor, such as a smart phone, or other computing device, such as a laptop or a PC, a wrist or smart watch, or an external device, such as an accelerometer

DETAILED DESCRIPTION OF THE INVENTION

The invention will be more clearly understood from the following description of some embodiments thereof, given by way of example only, with reference to the accompanying drawings, in which.

Figure 1:
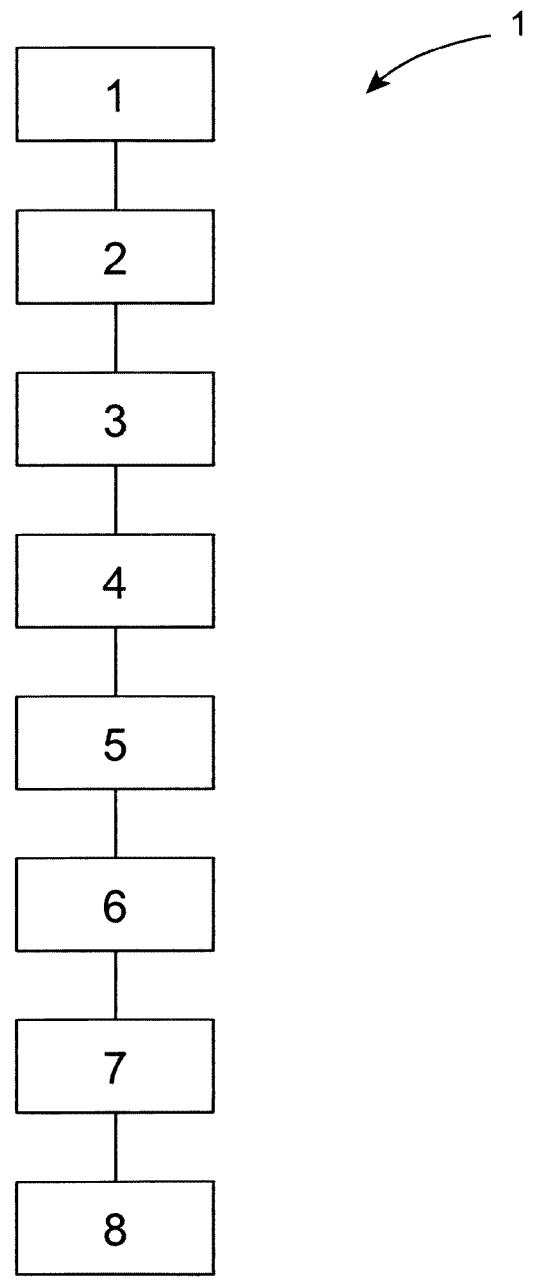
FIG. 1 is a flow diagram of the steps in a method for selecting an audio file and delivering the audio file to a mobile computing device according to the invention.

Referring to the drawings, and initially to FIG. 1, there is a flow diagram 1 showing the steps in a method for selecting an audio file from a mobile computing device connected to or held by a user, the computing device having or being communicatively coupled with motion sensors.

A plurality of audio files, each having audio content with a different predefined beat parameter, is stored optionally in a compressed format, and on storage means or in a library of the mobile computing device. The audio files may be downloaded to the mobile computing device from a remote computing device. Alternatively, the audio files may be stored in storage means of the remote computing device. The audio files may be, for example, in MP3 format or other audio format, and have beat parameters in the range of 5 beats per minute to 300 beats per minute, although it will be understood that audio files may be provided in any range of beats per minute as required or as desired.

At step 1 the mobile computing device is caused to move as a result of the user walking while the mobile computing device is connected to them in such a way that motion sensors of the mobile computing device may detect the motion of the user and generate motion data based on user movement. The motion sensors comprise or are provided as an accelerometer or other means operable to detect 3-axis acceleration or movement of the user.

At step 2, step data is computed from the motion data based on a number of steps taken by the user in a specific period of time, such as one, two, three, four or more minutes. At the conclusion of this initial specific period of time for collecting motion data a loud audible beeping sound may be triggered to let the user know that the initial period of time has passed.

At step 3, optionally, the step of computing the step data further comprises a step of calibrating the accelerometer according to one or more of reduced stride length, speed and cadence. This optional step uses the 3-axis (or X, Y, Z co-ordinates) of the accelerometer. The X, Y, Z, co-ordinates are identified and movement calibration is honed for specific gait issues that day, for example, reduced stride length, speed or cadence to enhance accuracy of system analysis. These adjustments allow for the system to not over or underestimate user movement which differs from an average healthy person who does not have PD. Standard settings may overestimate patients cadence (steps/min) and therefore must be adjusted daily to the user's PD symptoms and so may be performed at different times, such as first thing in the morning, in order to adapt the sensitivity of the mobile computing device.

Accordingly the present invention comprises a step of setting a sensitivity level for the motion sensors which comprises calibrating the motion sensors to detect steps of a user according to one or more of stride length, speed and cadence. The ability to adapt the sensitivity of the motion sensors in this way ensures that the present invention may be adapted to the specific gait requirements of a user so that steps having a smaller (or indeed larger) amplitude and/or stride length from a pre-determined level may be correctly sensed, which is important for patients suffering from Parkinson's disease. Such a step of setting a sensitivity level for the motion sensors may also be performed automatically by the mobile computing device.

At step 4, a metronome beat based on the step data is computed by recording the total number of steps walked in two minutes and the average number of steps per minute. To this step data, and in order to prescribe a user's optimum metronome beat for a day, one of the following computations is applied:

1. average baseline steps/min×1.1, or
2. average baseline steps/min×0.9

The standard algorithm applied will be the average baseline steps/min×1.1. However this may be adapted to average baseline steps/min×0.9 if the clinician remotely monitoring the user considers that this is desirable, such as due to a decreased stride length, to address gait deterioration in the user.

The patient will then be provided with their individually prescribed metronome beat, in beats per minute, for the day and, at step 5, a metronome beat file is generated. The metronome beat file may be generated by the mobile computing device or at a remote computing device to which the motion and/or step data has been transmitted from the mobile computing device. It will be understood that the metronome beat file thus encodes data or tags relating to the step data, including the metronome beat computed according to the above algorithm.

At step 6, a stored audio file having a predefined beat parameter in beats per minute matching the metronome beat of the metronome beat file is automatically selected. For example, if the metronome file generated includes a metronome beat computed as above of sixty beats per minute, then the audio file selected also has audio content including a metronome beat of sixty beats per minute. The sound wave of the audio file selected will match the metronome beat which has already been calculated in calibration.

At step 7, the audio file selected is played via audio output means so that the user may hear it. The audio output means may be provided as a speaker of the mobile computing device, a headphone system coupled to the mobile computing device, and/or as a separate audio output device adapted for the user. In this way the user receives via audio output means an individually prescribed metronome beat prescription as a treatment to override the dysfunction of the basal ganglia in the brain and generate the correct impulses (auditory cues) for overcoming symptoms externally so as to improve the quality of walking and prevent freezing episodes.

At step 8, the motion sensors of the mobile computing device again detect the motion of the user in response to the treatment provided at step 7, and this data is transmitted to the remote computer server, such as via a cloud computing network arrangement for review by qualified physiotherapists to identify deteriorations in real time and recommend the next steps to take in furthering treatment for the user.

The present invention may also use the motion sensors to detect a change in the motion of the user, and then use the detected change of motion to determine whether the user is suffering from a motion event relating to Parkinson's disease. Such a step involves detecting the deceleration rate of motion of the user, and then comparing the detected deceleration rate to a predetermined range of deceleration rates and if the detected deceleration rate falls within the predetermined range recording motion data relating to the detected deceleration. Such a motion event would indicate that the user has suffered a true Parkinson's freezing event, or alternatively if the detected deceleration rate falls outside the predetermined range, that the user has stopped stepping for other reasons not related to Parkinson's disease. The ability to utilise motion sensors such as are an accelerometer to detect deceleration rate would allow detection of a "true Parkinson's freeze" (a known Parkinson's symptom) as opposed to a standard stop. Such a "true Parkinson's freeze" would be sensed by the motion sensors as an immediate stop with limited deceleration, whereas a standard stop would be sensed by the motion sensors as having a gradual deceleration before coming to a stop.

The present invention also includes an automated voice training program. In operation, the patient is provided a word which they say aloud, and the sound has to reach a certain decibel level (such as that of average speech, which is 60 db). When the patient reaches this decibel level they will be provided further words, one at a time, until they have said ten words reaching 60 db each time. They will complete this training daily. Such training is very important since sufferers of Parkinson's disease lose their voice and as their voice quietens over time they perceive that they are shouting, when in fact they are whispering or talking at a normal level. This automated speech training will improve patient's speech by training patients to speak at the correct decibel levels.

Figure 2:
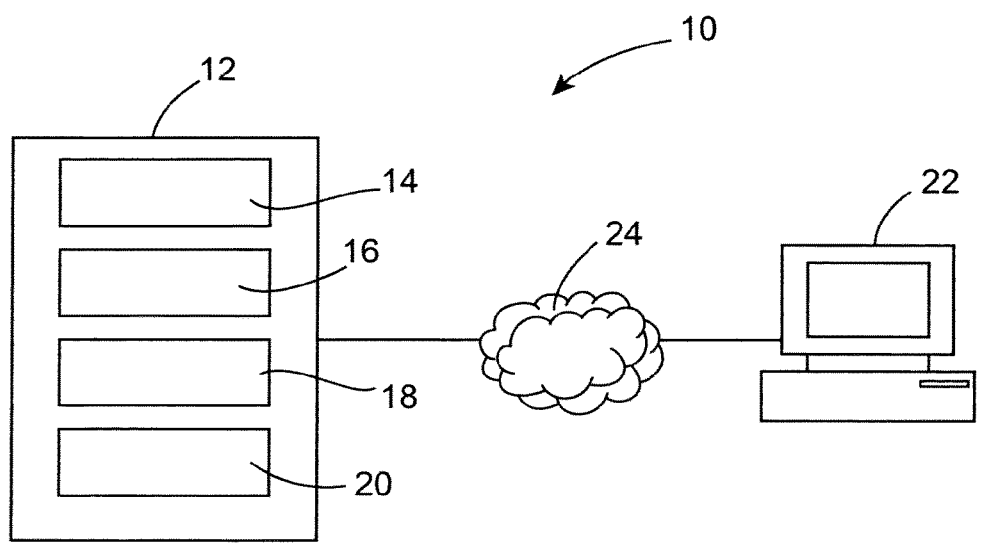
FIG. 2 is a stylised schematic of a system for selecting an audio file and delivering the audio file to a mobile computing device according to the invention.

Turning to FIG. 2 there is shown a system for implementing the method according to the present invention.

The system 10 comprises at least one mobile computing device 12, such as a smart phone or other computing device, such as a laptop or a PC, a wrist or smart watch, or an accelerometer or pedometer having computer processor means, and motion sensors 14 or motion detecting means integrated therein or associated therewith, and processor means 16 for obtaining motion data from the motion sensors and computing from the motion data step data based on a number of steps taken by a user in a specific period of time. Although FIG. 2 shows one mobile computing device 12, it will be understood that the present invention may comprise a plurality of such devices 12 coupled to a remote server computer 22 via internet 24.

The processor means 16 is further operable for computing a metronome beat based on the step data and generating a metronome beat file, and also for selecting from storage means 18 of the mobile computing device 12 a stored audio file having a predefined beat parameter matching the metronome beat of the metronome beat file.

The mobile computing device further comprises audio output means 20 for playing the audio file so that it may be heard by a user. It will be understood that the audio output means 20 may be a speaker integrated with the mobile computing device 12, or a headphone system coupled with the mobile computing device 12, and/or as a separate external audio output device adapted for the user to hear the audio file as it is being played. The present invention also envisages, as a mobile computing device, a pedometer having computer processor means and audio output means.

The present invention is implemented by computer software which is downloaded to mobile computing device 12 from a remote server computer 22 via a wired or wireless computer network, such as internet 24. The computer software implementing the present invention may be provided as a software application or app which when downloaded may be run on the processor means 16.

An exemplary implementation of the present invention will now be described with reference to FIGS. 3 to 16 which show screen displays of a user interface for an implementation on a mobile computing of the method according to FIG. 1.

Figure 3:
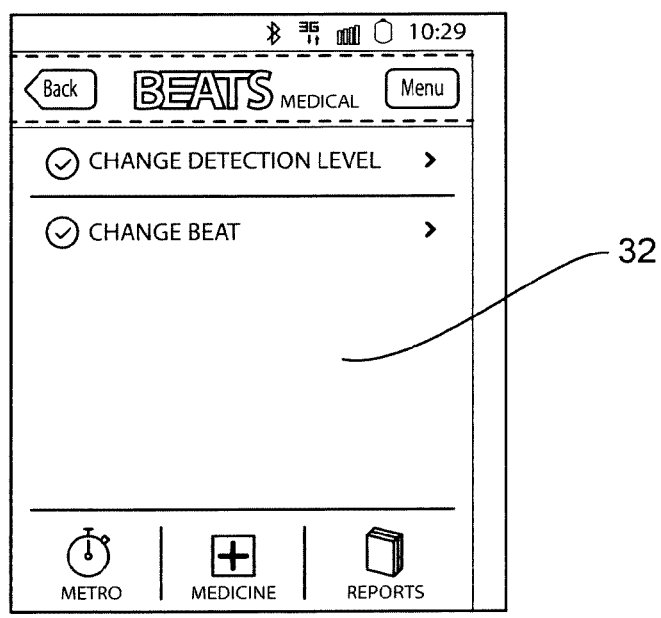
FIGS. 3 to 18 are screen displays of a user interface for an implementation on a mobile computing of the method according to FIG. 1.
Figure 4:
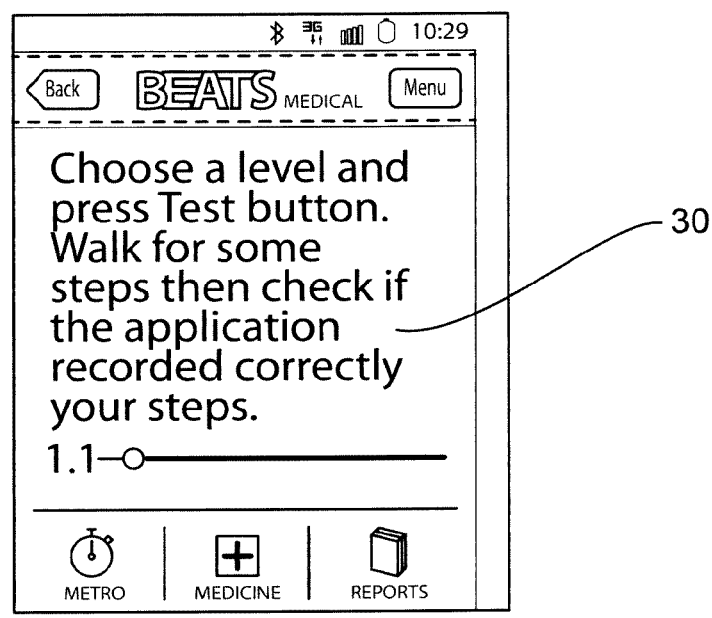

As shown in FIGS. 3 and 4, at screen's 30, 32 a user's walking is monitored and recorded and the sensitivity of their mobile computing device is adapted or calibrated to their walking through a sensitivity bar operable for setting a sensitivity level for the motion sensors. Such a sensitivity comprises means for calibrating the motion sensors to detect steps of a user according to one or more of stride length, speed and cadence. The ability to adapt the sensitivity of the motion sensors in this way ensures that the present invention may be adapted to the specific gait requirements of a user so that steps having a smaller (or indeed larger) amplitude and/or stride length from a pre-determined level may be correctly sensed, which is important for patients suffering from Parkinson's disease. Such a step of setting a sensitivity level for the motion sensors may also be performed automatically by the mobile computing device.

Figure 5:
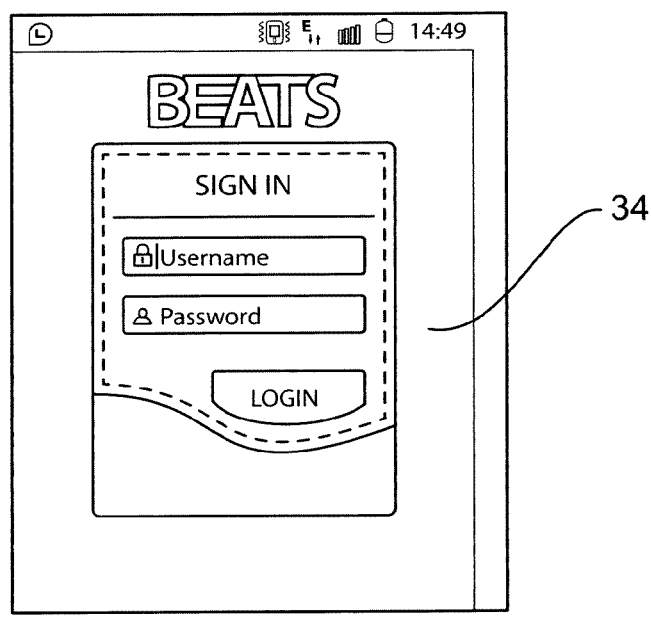
Figure 6:
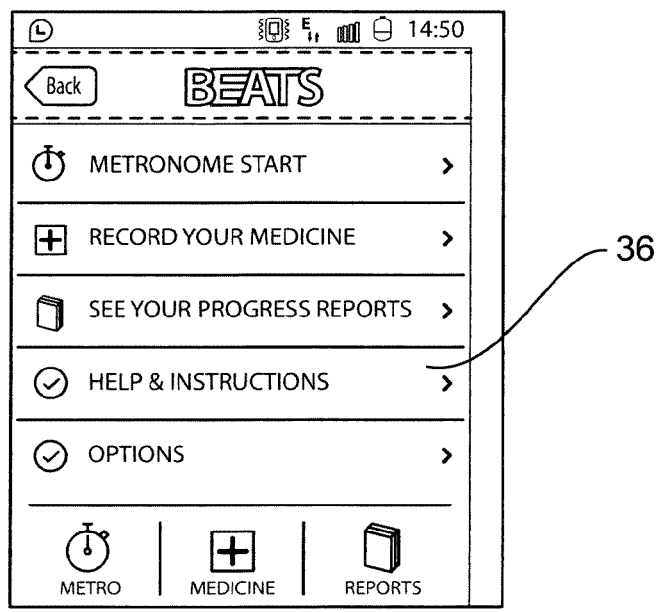

FIG. 5 shows a username and password screen 34, which when correctly filled in by a user will then provide access to the present invention via an app on their mobile phone. Each day the present invention may assess their mobility and prescribe the optimum metronome therapy based on their performance that day, the options for which are shown in FIG. 6 as screen 36.

Figure 7:
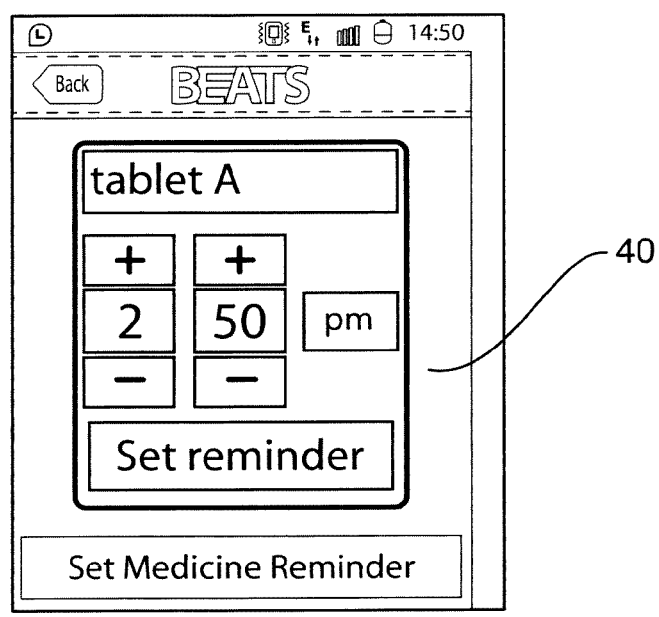
Figure 8:
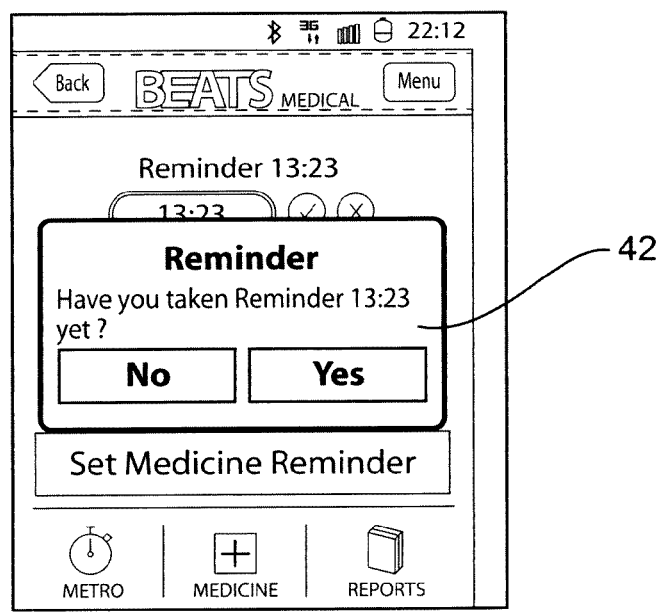

FIG. 7 shows a screen 40 via which a user may set up medication reminders so that set reminders will appear automatically, as shown in screen 42 in FIG. 8.

Figure 9:
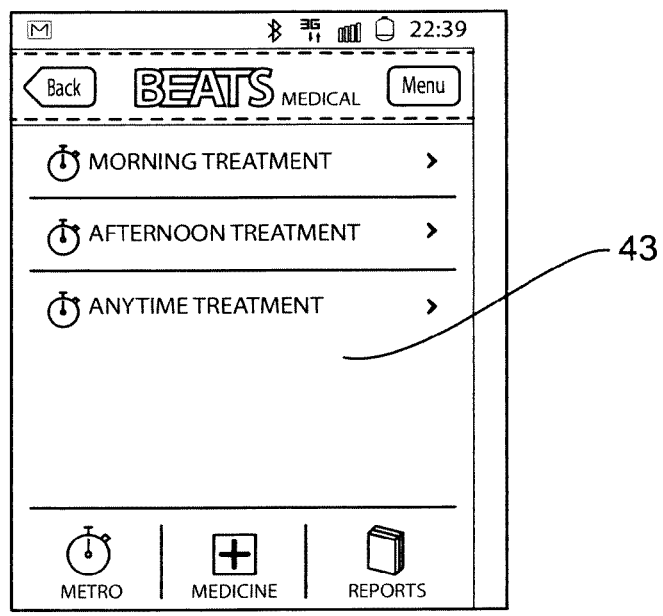
Figure 10:
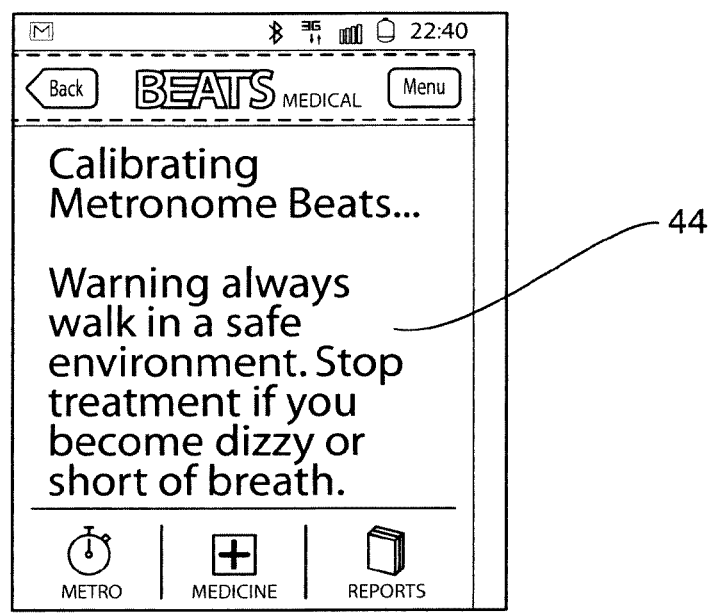
Figure 11:
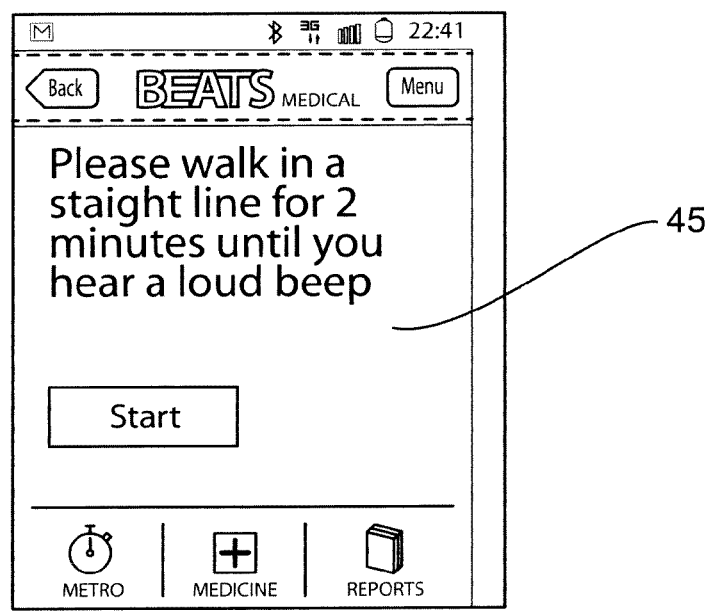

FIGS. 9 to 11 show screens 43, 44, 45 prompting a user to carry out a two minute walk test. In the instance shown the user is prompted to walk for two minutes with the app running on a mobile computing device at their waist band. The average number of steps per minute is also recorded. A computation is then applied to the results of this test to prescribe optimum metronome beat for that day to generate the required metronome beat file, the computation being one of:

1. average baseline steps/min×1.1, or
2. average baseline steps/min×0.9

Figure 12:
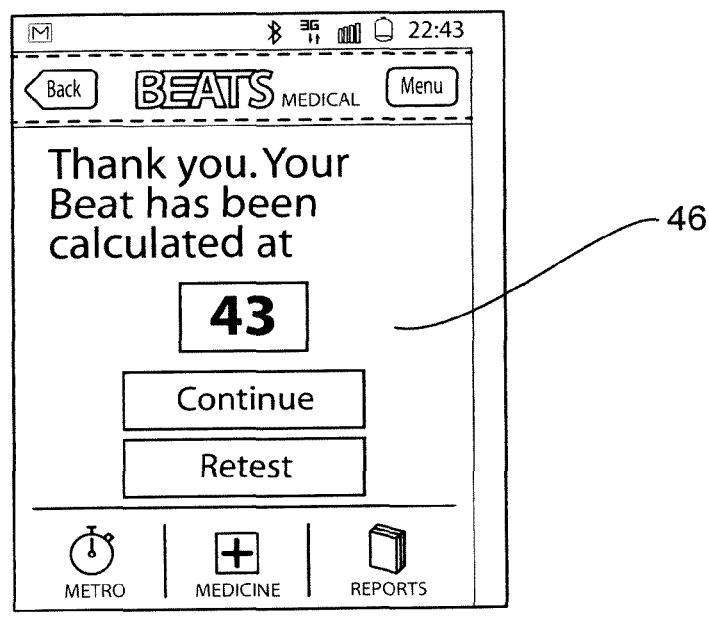

FIG. 12 shows screen 46 displaying the individually prescribed metronome beat for the day. In the instance shown the metronome beat has been calculated as 43.

A stored audio file having a predefined beat parameter in beats per minute matching the metronome beat of the metronome beat file is selected. For example, the metronome file generated in the present example includes a metronome beat computed as 43 beats per minute then the audio file selected also has a metronome beat of 43 beats per minute.

Figure 13:
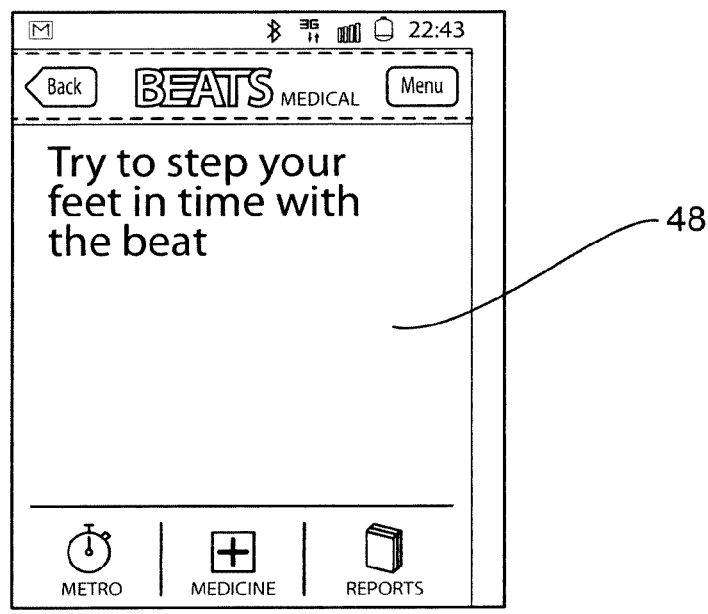

As shown in FIG. 13, screen 48 is displayed so that the user is prompted to move their feet in time with the audio file selected.

The audio file selected is played via a speaker of the mobile computing device so that the user may hear it and walk in time with the beat of the audio file. In this way the user has received via a speaker of the mobile computing device an individually prescribed metronome beat prescription as a treatment to override the dysfunction of the basal ganglia in the brain and generate the correct impulses (auditory cues) for overcoming symptoms externally so as to improve the quality of walking and prevent freezing episodes.

Figure 14:
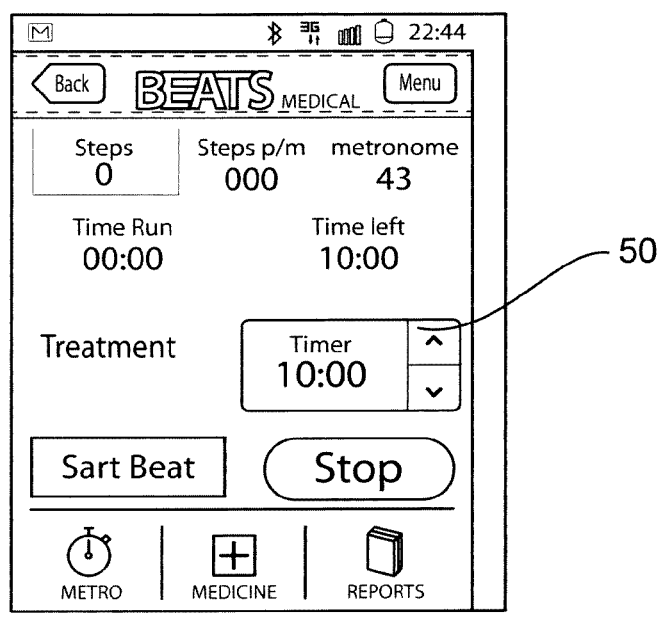
Figure 15:
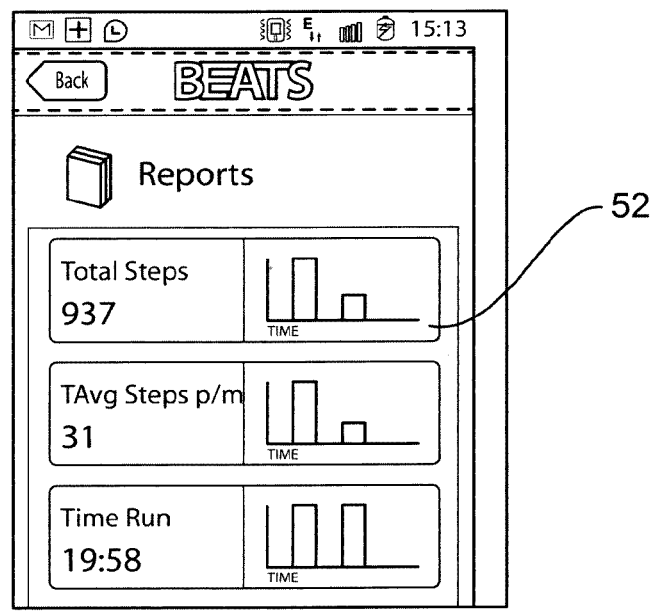
Figure 16:
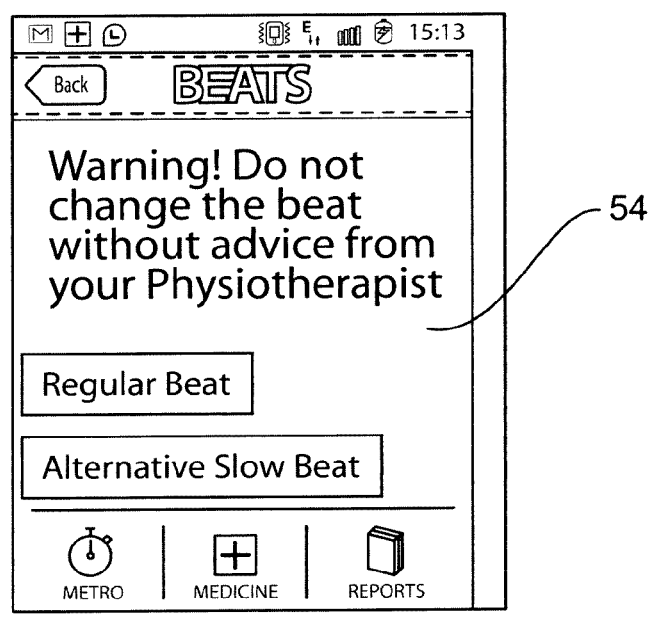
Figure 17:
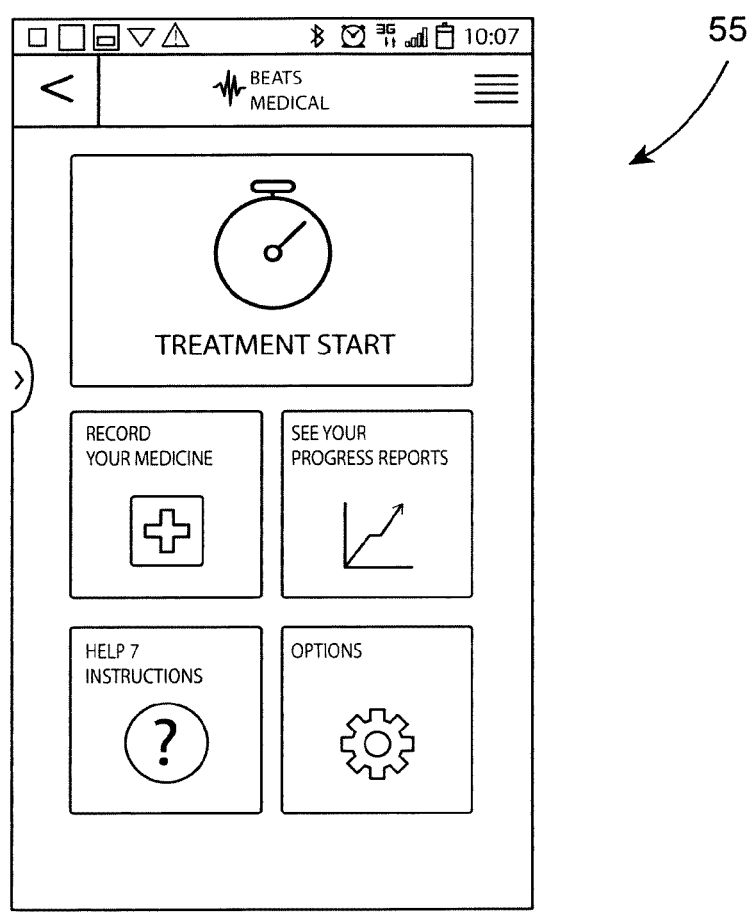
Figure 18:
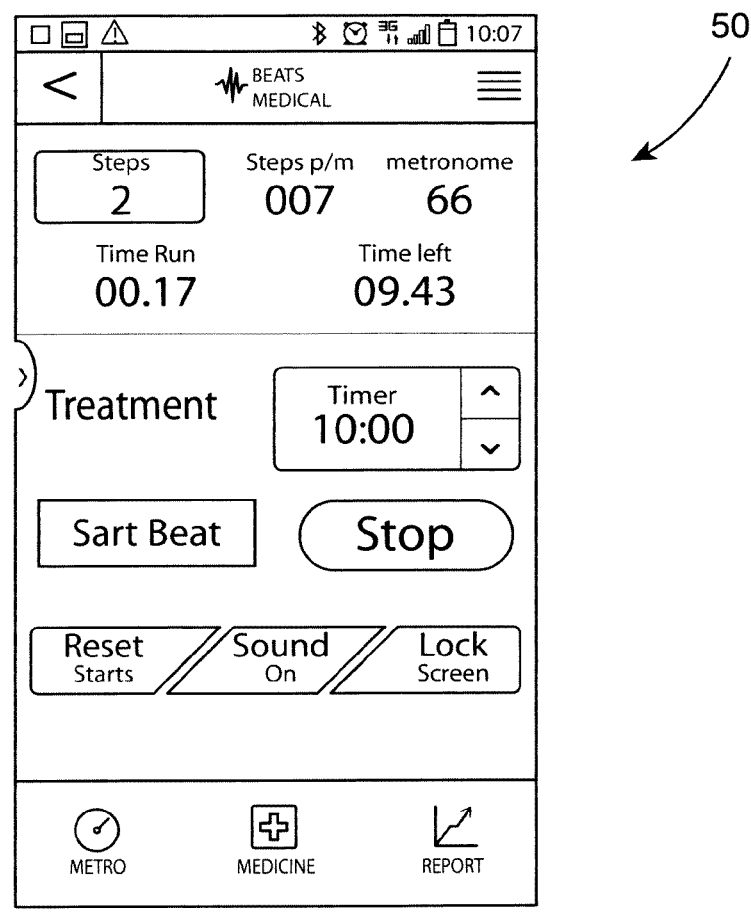

As shown in FIGS. 14 and 18, screen 50, the user may be provided with one or more ten minute metronome therapy sessions each day. An anytime option is also provided in which they can use a daily metronome beats prescription as needed. As shown in FIG. 15, screen 52, users may view their progress via reports that are displayed. Such reports may also be transmitted by email. A warning screen, such as that of FIG. 16, screen 54 may be displayed. FIG. 17 shows a home screen 55 for application software executing the present invention.

The present invention provides a technology solution delivered through a smart phone or other mobile computing device that improves the gait of people with PD. The user's daily mobility is assessed through a mobile computing device app and then calculates the required individually prescribed treatment for each user. The treatment is then delivered through audio output means, such as speakers of the mobile computing device in the form of auditory cueing.

The present invention provides an automated system which is made available to users via application software downloaded to a mobile computing device, such as a smart phone. Using the internal mobility sensors of a mobile computing device the present invention is operable to calculate automatically the required metronome therapy level and critically prescribe an audio cue designed specifically for that patient's current condition. This treatment is then delivered as an automatic audio track via the app and plays through the audio system of the mobile computing device. This mobility data is then sent to a remote computing server via wired or wireless connectivity means where it is assessed and the above specialised algorithms are applied.

The present invention has been shown to reduce episodes of freezing of gait (FOG), improves stride length, walking speed, reduces symptoms and improves overall quality of life.

Aspects of the present invention have been described by way of example only and it should be appreciate that additions and/or modifications may be made thereto without departing from the scope thereof as defined in the appended claims.

The invention claimed is:

1. A method of providing metronome therapy for a user who performs an activity with a cadence of movement by selecting a metronome audio file from a selection of metronome audio files accessed by a mobile computing device carried by the user during said activity, said method comprising the steps of:
   providing a mobile computing device that is operable to play said metronome audio files, wherein each of said audio files has corresponding audio beat parameters;
   providing at least one motion sensor operable to detect motion of the user at the mobile computing device, wherein said at least one motion sensor has a sensitivity setting;
   wherein when the user performs said activity with said cadence of movement said at least one motion sensor detects said cadence of movement;
   providing a sensitivity bar operable to adjust said sensitivity setting of said at least one motion sensor depending upon said cadence of movement by calibrating said at least one motion sensor to detect steps of a user according to said cadence of movement;
   configuring the at least one motion sensor to detect a deceleration in said cadence of movement by said user;
   detecting, identifying and recording changes in said cadence of movement that fall within a selected range of decelerations that are attributable to Parkinson's disease and generating motion data;
   using said motion data to generate a corresponding metronome beat;
   automatically selecting a specific metronome audio file from said metronome audio files on said mobile computing device by comparing said metronome beat to said audio beat parameters to find a best match; and
   providing the metronome therapy to the user by playing said specific metronome audio file on said mobile computing device that corresponds to said best match.

2. The method according to claim 1, further including applying a multiplication factor to said metronome beat prior to comparing said metronome beat to said audio beat parameters.

3. The method according to claim 1, wherein said audio beat parameters and said metronome beat are measured in beats per minute.

4. The method according to claim 1, further including the steps of providing a remote computing device and downloading said audio beat parameters and said metronome beat to said remote computing device.

5. The method according to claim 1, wherein said at least one motion sensor is selected from a group consisting of accelerometers and gyroscopes.

6. The method according to claim 1, wherein said cadence of movement is detected in each axis of a 3-axis reference frame of movement.

7. A system for providing metronome therapy for a user by selecting a metronome audio file from a selection of metronome audio files accessed by a mobile computing device carried by said user, said system comprising:

a mobile computing device operable to play said metronome audio files, wherein each of said metronome audio files has corresponding audio beat parameters;

at least one motion sensor to detect motion and deceleration of said user wherein said at least one motion sensor has a sensitivity setting and wherein when said user performs an activity with a cadence of movement, said at least one motion sensor detects said cadence of movement;

a sensitivity bar operable to adjust said sensitivity setting of said at least one motion sensor depending upon said cadence of movement by calibrating said at least one motion sensor to detect steps of said user according to said cadence of movement;

wherein said at least one motion sensor detects changes in said cadence of motion and said mobile computing device identifies and records if said changes in said cadence of motion are within a selected range of decelerations attributable to Parkinson's disease; and wherein said mobile computing device determines a metronome beat from said cadence of motion, automatically selects a specific metronome audio file from said metronome audio files by comparing said metronome beat to said audio beat parameters to find a best match, and plays said selected metronome audio file that corresponds to said best match.

8. The system according to claim 7, wherein said at least one motion sensor is contained within said mobile computing device and is adjusted by said mobile computing device.

9. The system according to claim 7, wherein a multiplication factor is applied to said metronome beat prior to comparing said metronome beat to said audio beat parameters.

10. The system according to claim 7, wherein said audio beat parameters and said metronome beat are measured in beats per minute.

11. The system according to claim 7, further including a remote computing device, wherein said metronome beat and said audio beat parameters are downloaded to said remote computing device.

12. The system according to claim 7, wherein said at least one motion sensor is selected from a group consisting of accelerometers and gyroscopes.

13. The system according to claim 7, wherein said cadence of movement is detected in each axis of a 3-axis reference frame of movement.

14. The method according to claim 1, wherein said sensitivity setting of said at least one motion sensor is automatically set.

15. The system according to claim 7, wherein said sensitivity setting of said at least one motion sensor is automatically set.

* * * * *